United States Patent [19]
Russell et al.

[11] Patent Number: 6,156,922
[45] Date of Patent: Dec. 5, 2000

[54] METHOD FOR THE SYNTHESIS OF AN AROMATIC DERIVATIVE ORTHO-DISUBSTITUTED BY A HALOGEN ATOM OTHER THAN FLUORINE AND BY A CYANO GROUP

[75] Inventors: James Russell, Rousson; Laurent Gilbert, Paris; Jean Pierre Maestro, Saint-Synphorien d'Ozon, all of France

[73] Assignee: Rhodia Chimie, Courbevoie, France

[21] Appl. No.: 09/101,034

[22] PCT Filed: Dec. 27, 1996

[86] PCT No.: PCT/FR96/02100

§ 371 Date: Sep. 15, 1998

§ 102(e) Date: Sep. 15, 1998

[87] PCT Pub. No.: WO97/24318

PCT Pub. Date: Jul. 10, 1997

[30] Foreign Application Priority Data

Dec. 28, 1995 [FR] France .................................. 95 15676

[51] Int. Cl.⁷ .................................................. C07C 253/00
[52] U.S. Cl. .............................................................. 558/343
[58] Field of Search .............................. 558/343; 546/286

[56] References Cited

FOREIGN PATENT DOCUMENTS

| 0 015 427 | 9/1980 | European Pat. Off. . |
| 0 097 357 | 1/1984 | European Pat. Off. . |
| 0 608 713 | 8/1994 | European Pat. Off. . |
| 2 353 516 | 12/1997 | France . |

OTHER PUBLICATIONS

Chemistry and Industry, Jan. 21, 1978, pp. 56–63, XP000601110, William Prescott, "The halogen exchange process for the production of fluoro–aromatics".

Journal of Fluorine Chemistry, vol. 61, 1993, pp. 193–216, XP000601952, V.M. Vlasov, "Flouride ion as a nucleophile and a leaving group in aromatic nucleophilic substitution reactions".

*Primary Examiner*—Cecilia Tsang
*Assistant Examiner*—Joseph Murray
*Attorney, Agent, or Firm*—Burns, Doane, Swecker & Mathis, L.L.P.

[57] ABSTRACT

The present invention relates to a method for the synthesis of a halogen substituted aryl nitrile, where the halogens are selected from Cl, Br, or I, by reacting an aryl dihalide with a halogen/fluoride exchange reactant to produce a halogen substituted aryl fluoride which is then reacted with a fluoride/cyanide exchange reactant to produce the halogen substituted aryl nitrile.

22 Claims, No Drawings

METHOD FOR THE SYNTHESIS OF AN AROMATIC DERIVATIVE ORTHO-DISUBSTITUTED BY A HALOGEN ATOM OTHER THAN FLUORINE AND BY A CYANO GROUP

The instant Application is a 371 of PCT/PR96/02100 filed Dec. 27, 1996.

The present invention relates to a method for the synthesis of an aromatic compound exhibiting an aromatic nucleus comprising at least one C—C unit substituted on a carbon atom by a cyano group and on the other carbon atom by a halogen atom other than fluorine.

The cyanation of halogenated aromatic compounds is known, the most widely used reaction being the Rosenmund-von Braun reaction, which achieves the cyanation of chlorinated or brominated aromatics in the presence of a stoichiometric amount of cuprous ions.

However, the industrial application of this reaction is very awkward and expensive because it requires effluent treatment operations for the purpose of separating copper salts and of possible recycling of the transition metal.

Furthermore, when the intended product is an aromatic compound carrying a cyano group ortho to a halogen substituent, the reaction to be carried out is a monocyanation of the corresponding orthodihalogenated aromatic. Now, the grafting of a nitrile functional group ortho to a halogen has a tendency to promote a second substitution to result in a dicyano, which is unfavourable to the reaction yield.

In addition, the copper-catalysed Rosenmund-von Braun reaction is generally not regioselective with respect to a specific halogen atom. However, a regioselective substitution of a halogen is often observed when the latter is ortho to an electron-withdrawing substituent with a predominant mesomeric effect, such as $NO_2$. In contrast, in the case of aromatic compounds with a nucleus depleted in electrons by an electron-withdrawing functional group with a predominant inductive effect, the orientation of the substitution is not very marked, much less than for nuclei depleted by an electron-withdrawing functional group by a mesomeric effect, and problems of regioselectivity can be posed.

The aim of the present invention is to overcome these disadvantages and to provide a method for the synthesis of such an aromatic derivative, disubstituted by a cyano group and a halogen atom arranged in the ortho position, which makes use of simple and inexpensive reactants, which does not require an effluent treatment operation and which results in the desired product with a good yield and good selectivity.

Surprisingly, the present Inventors have found that this aim, and others which will become apparent subsequently, can be achieved by a two-step method with great success, both from the yield viewpoint and from the viewpoint of selectivity, in comparison with the conventional single-step method.

In this respect, the subject-matter of the invention is a method for the synthesis of a compound of formula (I)

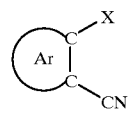

(I)

in which

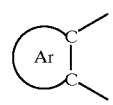

is an optionally substituted aromatic nucleus depleted in electrons containing at least five carbon-comprising ring members, and X is selected from Cl, Br and I, characterized in that it comprises at least the steps consisting in
(a) reacting a compound of formula (II)

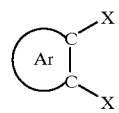

(II)

in which

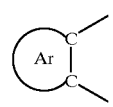

has the above meaning and the X substituents, which are identical or different, are selected from Cl, Br and I, with a fluoride-based halogen/fluorine exchange reactant, in order predominantly to form a compound of formula (III)

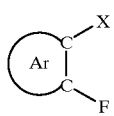

(III)

and
(b) reacting the reaction product of the step (a) with a cyanide-based fluorine/cyanide exchange reactant, in order selectively to form the compound of formula (I).

The reaction of the step (a) generally results in a major isomer of formula (III) and possibly in a minor isomer of formula (IIIb),

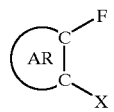

(IIIb)

by monosubstitution by a fluorine atom. It is even possible to observe very good regioselectivity depending on the nature of the compound of formula (II), in particular as a function of other possible substituents of the aromatic nucleus and of the position of the latter. This will be described in detail subsequently.

The reaction product of the step (a) can, however, comprise a mixture of isomers, the separation of which is technically very difficult and expensive to implement on an industrial scale.

Surprisingly, the reaction of the step (b) shows very high chemoselectivity which enhances the selectivity of the overall synthetic sequence in favour of the cyanation product of the isomer of formula (III) and which is unfavourable to the cyanation of the isomer of formula (IIIb). Thus, the step (b) can be carried out on the reaction mixture of the step (a) without separation of the isomers.

In addition, the product of the double cyanation of the compound of formula (III) is not observed and the desired product is obtained with very good selectivity.

The method of the invention preferably applies to compounds of formula (II) where the two X substituents are identical. Advantageously, each X is a chlorine atom.

Generally, it is preferable for at least one X to be a chlorine atom.

The aromatic nucleus

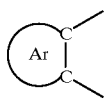

advantageously comprises 6 ring members and is in particular a benzene nucleus. It can also comprise at least one heteroatom.

The possible substituents of the aromatic nucleus can be highly varied in nature, for example carriers of functional groups of use in the continuation of the synthetic sequence. They can also be optionally substituted alkyl, alkenyl, alkynyl or aryl groups or alkenylene or alkynylene groups connected to the aromatic nucleus in order to form a polycyclic system comprising at least one aromatic nucleus. Mention may be made, as example of such a nucleus, of a naphthalene nucleus.

The aromatic nucleus of the compound of formula (II) is depleted in electrons due to the presence of the two X substituents. In addition, it can be depleted in electrons by an electron-withdrawing functional group forming a ring member of the said nucleus or by the presence of at least one substituent carrying an electron-withdrawing functional group grafted onto an atom of the said nucleus, or by both these causes simultaneously.

In particular, in the formula (II),

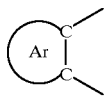

can be an aromatic nucleus comprising at least one heteroatom which depletes in electrons the aromatic nucleus, such as, in particular, nitrogen or phosphorus.

Mention may be made, as examples of such aromatic nuclei, of pyridine or quinoline.

The depletion in electrons can also result from the substitution of the said nucleus by at least one electron-withdrawing group.

Such an electron-withdrawing substituent can be selected from groups which withdraw by an inductive effect or by a mesomeric effect, as defined in the reference work in Organic Chemistry "Advanced Organic Chemistry" by M. J. March, 3rd edition, published by Wiley, 1985, in particular pages 17 and 238. It is preferable, in particular, to avoid groups carrying a hydrogen atom capable of forming hydrogen bonds, such as a carboxylic acid group, and groups carrying a basic hydrogen atom which can result in a deprotonation, such as an alkyl ketone group having a hydrogen α to the carbonyl.

Mention may be made, as example of suitable electron-withdrawing groups, of the groups —$NO_2$; —CN; —$CF_2R$ where R is a fluorine atom or a hydrocarbon-comprising radical; —COOR' where R' is a hydrocarbon-comprising radical; —CHO; —Cl; or —Br.

The method of the invention applies particularly advantageously to compounds of formula (II) in which the electron-depleted aromatic nucleus carries an electron-withdrawing substituent with a predominant inductive effect, these compounds giving poor results in the direct reaction of Rosenmund-von Braun type.

Such a substituent is preferably selected from —CN and —$CF_2R$ groups, where R is selected from a fluorine atom and hydrocarbon-comprising groups, advantageously $C_{1-20}$ hydrocarbon-comprising groups, which preferably are themselves electron-withdrawing. These hydrocarbon-comprising groups advantageously do not comprise a basic hydrogen atom which can result in a deprotonation.

A substituent of formula —$CY_2R$, where Y, which are identical of different, are selected from Cl and F and R has the above meaning or is a chlorine atom, can also be used but is capable of reacting in the step (a) to result in chlorine/fluorine exchange.

The said electron-depleted aromatic nucleus advantageously carries only a single electron-withdrawing substituent. Preferably, on a 6-membered aromatic nucleus, this substituent is found in the ortho or para position with respect to the X atom which is intended to be substituted in a first step by a fluorine atom in the step (a) to form the major product of formula (III). The presence of such an electron-withdrawing group ortho or para to this X atom has the effect of increasing the selectivity of the substitution reaction of the step (a), so that the product of formula (III) is greatly in the majority with, respect to the product of formula (IIIb), according to the following reactions:

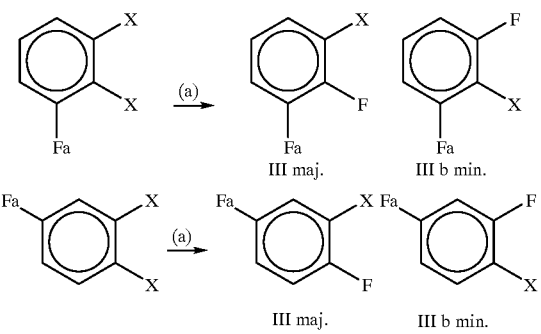

Preferably, when the said aromatic nucleus is an aryl, its electron density is at most in the region of that of a halobenzene, in particular of a dichlorobenzene.

To obtain satisfactory electron depletion, it is preferable for the sum of the Hammett constants of the electron-withdrawing functional groups carried by the said aromatic nucleus, either as ring member or as substituent of the said nucleus, to be between 0.10 and 1.60.

More particularly, it is advantageous for the sum of the Hammett constants of the substituents of the said aromatic nucleus to be between 0.4 and 1, advantageously from 0.5 to 0.8.

In addition, it is advantageous for each substituent other than X to have a Hammett constant of between 0.2 and 0.7.

For the definition of Hammett constants, reference will be made to the reference work: March—"Advanced Organic Chemistry", third edition, John Wiley and Son, pages 242 to 250.

By way of example, the method of the invention can be employed with 3,4-dichlorotrifluoromethylbenzene in order to synthesize 2-chloro-4-(trifluoromethyl)benzonitrile, with a good yield and high selectivity, according to the scheme hereinbelow.

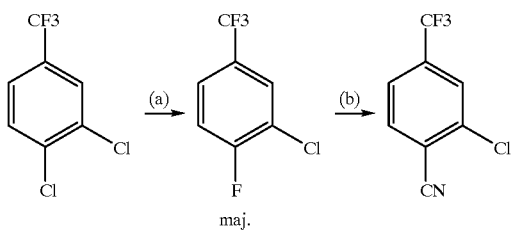

maj.

The method of the invention comprises essentially two steps.

In a first step (a), the compound of formula (II) is reacted with a halogen/fluorine exchange reactant. This reactant is advantageously an inorganic fluoride, preferably selected from alkali metal fluorides, in particular, from sodium fluoride, potassium fluoride, rubidium fluoride and caesium fluoride. Potassium fluoride is generally preferred for economic reasons, although fluorides of alkali metals with an atomic mass greater than that of potassium substantially Strove the reaction yield.

It is also possible to use, as counterceration of the fluoride, any cation having properties equivalent to those of an alkaline cation, such as, for example, a quaternary ammonium cation.

Numerous methods have been described for carrying out this reaction, such as, for example, those disclosed in the certificate of addition U.S. Pat. No. 2,353,516 and in the article Chem. Ind. (1978), 56, and have been employed industrially for producing aryl fluorides, aryls on which are grafted electron-withdrawing groups.

This reaction can be carried out by heating the reaction components at a relatively high temperature, generally from 200 to 280° C., in particular in the region of 250° C., in an appropriate solvent.

In an alternative form, the reaction can be carried out at lower temperature, with a significant improvement in the yield, by subjecting the reaction mixture to the action of ultrasound.

Generally, the reaction can be carried out at a temperature of 80 to 280° C., according to the conditions chosen.

It should be pointed out that the use of ultrasound releases a large amount of energy within the reaction mixture; this energy substitutes, in all or part, for the heating energy normally required.

The preferred conditions comprise an ultrasound power emitted directly by the wall providing for this emission at least at 20 W/cm$^2$, advantageously to 50 W/cm$^2$, more advantageously to 100 W/cm$^2$, preferably to 200 W/cm$^2$.

The frequencies which can be used are those of commercial devices, that is to say that the frequency of the ultrasound is advantageously between 10 and 100 KHz, preferably between 15 and 50. Some frequencies give very significantly better results; they correspond to those of resonance of the mixture under the conditions of the experiment and are generally covered by the relatively broad emission spectrum of commercial devices.

The use of ultrasound makes it possible to carry out the reaction at relatively low temperatures of between 80 and 200° C., preferably from 100 to 150° C.

Generally, the reaction preferably takes place in a dipolar aprotic solvent. The relative dielectric constant $\in$ of the said solvent is advantageously at least equal to 10, preferably $\in$ is less than or equal to 100 and greater than or equal to 25. Preference is particularly given to solvents for which the donor number D, expressed by the variation in enthalpy (ΔH in kcal/mol) of the combination of the said solvent with antimony pentachloride, is from 10 to 50.

Advantageous solvents are dimethyl sulphoxide (DMSO), dimethyl sulphone, dimethylformamide (DMF), N-methylpyrrolidone (NMP), dimethylacetamide (DMAC) and sulpholane (tetramethylene sulphone).

The halogen/fluorine exchange reactant advantageously comprises a solid which remains in the form of a solid dispersed in the reaction mixture and which comprises an alkaline fluoride and optionally a cation which promotes the reaction.

The reactant advantageously comprises, as promoter, a heavier alkaline cation than potassium. This alkaline cation can be introduced in the form of a halide and not necessarily in the form of a fluoride. In general, the alkaline cation is introduced in the form of a chloride. The content of alkaline cation advantageously represents from 1 to 5 mol %, preferably from 2 to 3 mol %, of the fluoride used.

The reaction can comprise, as promoter, agents often described as phase transfer agents and which are "oniums". The oniums generally represent from 1 to 10 mol %, preferably from 2 to 5 mol %, of the fluoride.

The oniums are selected from the group of cations formed by elements from Groups VB and VIB (as defined in the Table of Periodic Classification of the Elements published in the supplement to the Bulletin de la Société Chimique de France in January 1966), with 4 or 3 hydrocarbon-comprising chains.

Among oniums deriving from elements from Group VB, the preferred reactants are tetraalkyl- or tetraarylammonium or -phosphonium not exhibiting hydrogen β to the heteroatom. The hydrocarbon-comprising group advantageously comprises from 4 to 12 carbon atoms, preferably from 4 to 8 carbon atoms. Mention may be made, for example, of tetramethylammonium or tetraphenylphosphonium. It is also possible to use compounds of alkylpyridinium type. Oniums deriving from Group VIB are preferably derived from elements with an atomic number greater than that of oxygen.

The ultrasound method described above makes it possible advantageously to use tetraalkylammonium, which have little stability at a temperature greater than approximately 150° C.

The amount of onium generally represents from 1 to 10%, preferably from 2 to 5%, of the mass of the inorganic fluoride.

In general, the molar ratio of the said alkaline or ammonium fluoride to the said substrate is between 0.8 and 1.5, preferably in the region of 1.25 times the stoichiometry. It can be advantageous to operate with a substoichiometric fluoride/substrate ratio (thus an incomplete conversion) because the risks of a double halogen/fluorine exchange reaction capable of taking place when the compound of formula (I) is in the presence of a large excess of fluorine are thus limited and, under these conditions, the compound of formula (I) is formed with an excellent selectivity which improves the selectivity of the overall method.

It is also desirable for the water content of the reactant to be at most equal to approximately 2%, preferably 1%, with respect to the mass of the reactant.

Stirring is advantageously carried but so that at least 80%, preferably at least 90%, of the solids are maintained in suspension by the stirring.

In fact, it is desirable for the greater part of the solids to be in suspension in the reaction mixture.

Thus, the stirring, to meet this restriction, must be neither too vigorous, in order to avoid pressing, by cyclone effects, an excessively large portion of the solids against the wall of the reactor, nor too low, in order to be capable of causing the solids resulting from the reaction and the solids used as fluorine source to pass into suspension.

The reaction product from the step (a) can be charged in the step (b) as soon as the progress of the first step is deemed to be satisfactory.

"Reaction product" is understood to mean the product of the substitution reaction of a halogen atom by a fluorine atom on the compound of formula (II). This reaction product generally comprises a mixture of isomers resulting from the substitution of one or other of the X atoms and a very minor amount of difluorination product resulting from the substitution of both X atoms, this reaction product predominantly containing the compound of formula (III).

According to the invention, the separation of the reaction product from the reactants which have not been converted during the step (a) is unnecessary because they will not be affected by the reactant of the step (b), or else to only a very small extent, to optionally provide desired product of formula (I). Neither is any attempt made to isolate the products formed and still less the monofluorination isomers.

The reaction mixture obtained at the end of the step (a) can thus be charged as is in the step (b).

Generally, the reaction product, optionally in solution in all or part of the solvent used for the reaction of the step (a), is charged in the step (b) in the form of a mixture with a fluorine/cyanide exchange reactant.

This reactant advantageously comprises a cyanide selected from cyanides of metals from Groups I and II, such as, in particular, sodium, potassium, magnesium or calcium, and quaternary ammonium cyanides. Sodium cyanide and potassium cyanide are among the preferred reactants. It is also possible advantageously to use a mixture of potassium cyanide and of calcium chloride, source of calcium cyanide.

The amount of exchange reactant, expressed as mols of cyanide, employed in the step (b) is preferably between 1 and 2 times, advantageously between 1 and 1.5 times, the amount of compound of formula (II) formed in the step (a).

The reaction components are preferably brought together in a polar aprotic solvent. The relative dielectric constant $\in$ of the said solvent is advantageously at least equal to 10, preferably $\in$ is less than or equal to 100 and greater than or equal to 25. Preference is particularly given to solvents for which the donor number D ($\Delta H$ in kcal/mol of the combination of the said solvent with antimony pentachloride) is from 10 to 50.

The majority of the solvents which can be used in the step (b) are also valid for the step (a). Thus it is that the reaction product of the step (a) can be introduced into the step (b) in its reaction solvent, which does away with any intermediate operation between the steps.

The solvent which can be used for the step (b) can, without problem, be selected from those having a dielectric constant and/or a donor number of the order of the low limits indicated above, indeed lower than these limits (solvents of little or very little polarity), such as, for example, acetonitrile, benzonitrile or crown ethers, allowing for the additional use of phase transfer agents, such as the "oniums" described previously.

The reaction temperature depends on the nature of the cyanide-based reactant and the solvent. Generally, a temperature rise accelerates the reaction. The reaction is advantageously carried out between 20 and 250° C.

The reaction takes place readily at atmospheric pressure in a conventional reactor but can also take place in a pressurized reactor, advantageously at a pressure of less than $5 \times 10^6$ Pa.

It is preferable for the reaction mixture to be substantially anhydrous, not only in order to maintain the selectivity of the reaction in favour of the desired isomer but also to limit the corrosion due to the fluoride ions released as reaction by-product.

The presence of a transition metal, in particular copper, in the reaction mixture in the step (b) is not advantageous because the reaction takes place spontaneously. It is even desirable to operate with a copper content as low as possible in order to avoid corresponding separation and retreatment operations.

The copper content in the reaction system of the step (b) is preferably $10^{-2}$ mol.l$^{-1}$ or less. Advantageously, this content is less than $10^{-3}$ mol.l$^{-1}$, preferably than $10^{-4}$ mol.l$^{-1}$.

The copper content can also be expressed with respect to the amount of the substrate in the reaction of the step (b). In this case, it is preferable for the amount of copper present in the reaction system of the step (b), expressed as mol, to be less than one tenth, advantageously than one hundredth, very particularly than one thousandth, of the amount of reaction product employed in the step (b), expressed as mol.

The duration of the reaction is determined as a function of the rate of formation of the desired final isomer.

The desired final product of formula (I) present in the reaction mixture at the end of the step (b) can easily be isolated. The separation technique preferably comprises the following two operations:
  filtration or distillation, in order to separate the organic compounds from the inorganic salts,
  fractional distillation, in order to separate, from the said organic compounds, the desired product of formula (I), the reactants and reaction products from the step (a) which have not reacted in step (b), and the solvent.

The method according to the invention can comprise the operations consisting in:
  i) mixing the compound of formula (II) and the X/F exchange reactant in a solvent;
  ii) subjecting the mixture thus obtained to heating or to an ultrasound emission;
  iii) optionally separating the solid phase and/or at least a portion of the solvent from the reaction mixture obtained in (ii);
  iv) adding, to the reaction mixture of ii) or to the residue of the operation (iii), the F/CN exchange reactant, optionally with an amount of a solvent identical to or different from that of the operation (i);
  v) maintaining the contact between the reactants, optionally while raising the temperature of the mixture;
  vi) separating, from the reaction mixture obtained in (v), the solid phase based on inorganic salts;
  vii) separating the compound of formula (I) from the remaining liquid phase by fractional distillation.

The inorganic salts separated in (vi) include the unreacted reactant of the operation (i) and salts formed by the fluoride ions released by the reaction at the operation (v). These salts can advantageously be recycled in the step (i) in order to be used therein as halogen/fluorine exchange reactant.

As was said above, the two-step method according to the invention provides the desired product with a very good yield. The high selectivity of the second step, which could not be anticipated and has been demonstrated by the present inventors, makes it possible directly to treat the reaction mixture obtained in the step (a) in order to obtain, on conclusion of the step (b), a reaction product comprising essentially the desired compound of formula (I).

In fact, the two-step method is easy to implement in the context of industrial scale production, in so far as it only requires conventional equipment, if necessary comprising a unit for separation of the intermediates which is particularly simple, and in so far as it makes it possible to dispense with effluent retreatment units intended to recover salts of transition metals, such as copper, which are essential in a plant for production by the conventional single-step method.

Furthermore, the cyanation step (b) uses a reactant which is economical, on the one hand, by the low cost of the cyanide salts and, on the other hand, by the absence of transition metal.

The invention will now be illustrated by the following examples, which exhibit various reaction conditions which allow the synthesis of 2-chloro-4-(trifluoromethyl) benzonitrile

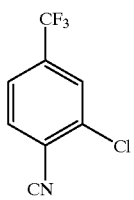

which is an intermediate of use in the preparation of herbicides, in two steps from 3,4-dichlorotrifluoromethylbenzene.

The results presented in the examples are expressed as a function of three quantities which are defined hereinbelow:
the degree of conversion of a reactant R (DCR) is the ratio of the amount (molar) of R which has disappeared during a reaction to the initial amount of R;
the real production yield of a product P from a reactant R (RYP) is the ratio of the amount of P produced to the initial amount of R;
the conversion yield of R to P (CYP), which is the ratio of the amount of P produced to the amount of R which has disappeared.

EXAMPLE 1

A—Synthesis of 3-chloro-4-fluorotrifluoromethylbenzene

The following reaction is carried out:

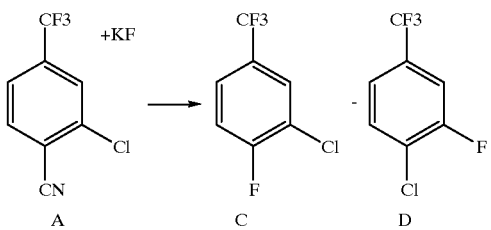

35.4 g (0.164 mol) of 3,4-dichlorotrifluoromethylbenzene A, 11.6 g (0.200 mol) of potassium fluoride, 2.8 g (0.008 mol) of tetra(n-butyl)phosphonium bromide and 44.0 g of sulpholane are introduced at room temperature, in an anhydrous atmosphere, into a glass reactor equipped with a mechanical stirrer, a fractionation column and a reflux condenser.

The reaction mixture is heated and the temperature is maintained at 85±2° C.

Distillation begins after approximately 30 minutes and, after a rapid development, gradually slows down. The reaction is complete after 5 hours.

The mixture is purified by fractional distillation in order to recover the aromatic fractions and the sulpholane.

The conversion of A is DCA=82.2%

The real yield of C is RYC=66.3%, the conversion yield of A to C, CYC, has the value 80.7%.

The real yield of D is RYD advantageously 8.0%, the conversion yield of A to D has the value 9.7%, The conversion thus takes place with an 89% selectivity in favour of C and an 11% selectivity in favour of D.

B—B synthesis of 2-chloro-4-(trifluoromethyl)-benzonitrile

The following are placed in a reactor:
1 g of the mixture of isomers C and D separated in A (1 mol equivalent)
16.1 g of DMSO (41 mol equivalents)
0.52 g of KCN (1.6 mol equivalents)

The reaction mixture is heated at a temperature of 60° C. for 10 h 15 minutes.

Analysis of the final reaction mixture makes it possible to determine that the reaction corresponds to the following equation with the following results:

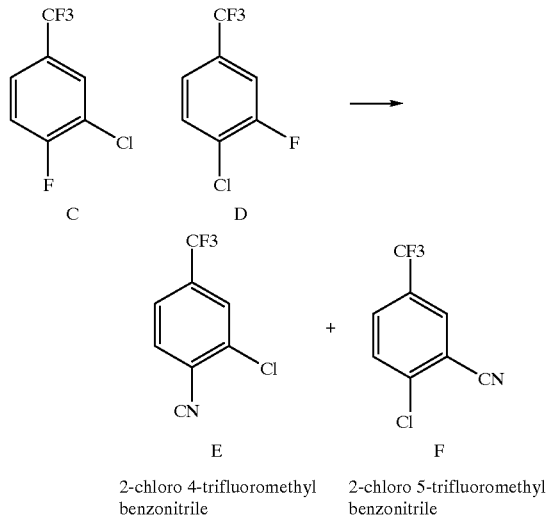

2-chloro 4-trifluoromethyl benzonitrile   2-chloro 5-trifluoromethyl benzonitrile

DCC=94%; DCD=35%; RYE=77%; RYF 11%; CYE=82%; CYF=31%.

C is converted virtually quantitatively (DCC=94%), whereas D is converted to only a small extent (DCD=35%). The reaction is highly regioselective.

Furthermore, the conversion of C results mainly in the desired product E (CYE=82%), whereas the conversion of D provides only a small amount of fluorine/cyanide exchange product F (CYF=31%).

Consequently, the cyanation reaction provides the desired product very selectively with respect to its isomer. In fact, the proportion of the desired isomer E with respect to the cyanation product (E and F), expressed by the molar ratio $$\frac{\text{amount of } E \text{ produced}}{\text{amount of } E + \text{amount of } F \text{ produced}} \text{ or } \frac{E}{E+F}$$

which is indicative of the regioselectivity of the reaction, is 98%. As the desired product is very slightly contaminated by its isomer, from which it is difficult to separate, it is sufficient to employ simple separation techniques in order to separate the other reaction by-products and provide a chlorocyanotrifluoromethylbenzene derivative of high purity which can be used directly for the purpose of subsequent conversions.

EXAMPLE 2

The step A is carried out as in Example 1 in order to obtain a monofluorination product comprising 89% of C and 11% of D.

The step B is carried out in the presence of 1.4 mol equivalents of sodium cyanide in DMSO (27 mol equivalents) at a temperature of 90° C. for 2 h 30 min.

The results of the cyanation are presented in the following Table 1, in which the operating conditions are summarized.

EXAMPLE 3 to 5

The steps A and B of Example 1 were repeated, apart from slight operating variations which mainly relate to the solvent, the temperature and the duration of reaction of the step B. The results are presented in Table 1.

These examples show that it is possible to vary the operating conditions according to the various preferred alternative forms indicated above while still obtaining very good results as regards the yield and the selectivity, in particular if the solvent is DMF or DMSO. Sulpholane requires slightly severer reaction conditions.

EXAMPLE 6

The step B of Example 1 was repeated on the pure product C (monofluorination product comprising 100% of C) with a cyanation reactant comprising a mixture of KCN and CaCl$_2$ in the proportion of 1.5 molar equivalents of KCN and 0.5 molar equivalent of CaCl$_2$ per one molar equivalent of C.

The degree of conversion and the conversion results are presented in Table 1, in which the operating conditions are recalled. The conversion is slightly lower than in Example 1 but the conversion yield is higher, so that the yield of the desired reaction is comparable with that of Example 1.

EXAMPLE 7

The step B of Example 1 was repeated on the pure product C with 1.5 molar equivalents of sodium cyanide NaCN in N-methylpyrrolidone (16 molar equivalents). Like sulpholane, NMP requires relatively severe conditions. However, a very good conversion and a satisfactory reaction yield are obtained.

The data of this example are collated in Table 1.

EXAMPLE 8

The step B of Example 1 was repeated on the pure product C with 1.9 molar equivalents of KCN in acetonitrile (11 molar equivalents) in the presence of tetrabutylammonium bromide as phase transfer agent (0.08 molar equivalent).

The results of this test, presented in Table 1 with the operating conditions, are once again highly satisfactory.

TABLE I

| | STEP A | STEP B | | | | | | | | E |
|---|---|---|---|---|---|---|---|---|---|---|
| Example No. | C/D Ratio | Solvent (eq.) | Reactant (eq.) | Temperature (° C.) | Duration (h) | DCC % | DCD % | RYE % | CYE % | $\frac{E}{E+E}$ % |
| 1 | 87/13 | DMSO (41) | KCN (1.6) | 60 | 10.25 | 94 | 35 | 77 | 82 | 98 |
| 2 | 89/11 | DMSO (27) | NaCN (1.4) | 90 | 2.5 | 97 | 27 | 79 | 81 | 98 |
| 3 | 89/11 | DMF (22) | KCN (1.8) | 80 | 13 | 90 | 53 | 71 | 79 | 98 |
| 4 | 90/10 | DMF (37) | KCN (1.7) | 60 | 30 | 85 | 32 | 66 | 80 | 99 |
| 5 | 89/11 | Sulpholane (56) | KCN (1.7) | 100 | 13.5 | 88 | 43 | 65 | 73 | 99 |
| 6 | 100/0 | DMF (32) | KCN (1.5) + CaCl$_2$ (0.5) | 80 | 10.35 | 88 | — | 76 | 86 | — |
| 7 | 100/0 | NMP (16) | NaCN (1.5) | 105 | 4.5 | 96 | — | 70 | 73 | — |
| 8 | 100/0 | MeCN (11) | KCN (1.9) + Bu$_4$N$^+$Br$^-$ (0.08) | 82 | 30.0 | 94 | — | 63 | 66 | — |

What is claimed is:

1. Method for the synthesis of a compound of formula (I)

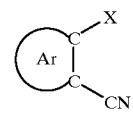

(I)

in which

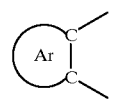

is an optionally substituted six-membered aromatic nucleus depleted in electrons, said nucleus comprising at least five carbon atoms, and X is selected from Cl, Br and I, characterized in that it comprises at least the steps comprising (a) reacting a compound of formula (II)

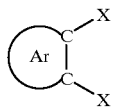
(II)

in which

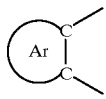

has the above meaning and the X substituents, which are identical or different, are selected from Cl, Br and I, with a fluoride-based fluorine/halogen exchange reactant, the reaction resulting in a compound of formula (III)

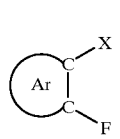
(III)

present as the major product in the reaction mixture, and
(b) reacting the reaction product from the step (a) directly with a cyanide-based fluorine/cyanide exchange reactant to form, the compound of formula (I).

2. Method according to claim 1, wherein, in the compound of formula (II), the two X substituents are identical.

3. Method according to claim 2, wherein each X represents a chlorine atom.

4. Method according to claim 1, wherein, in the compound of formula (II), is an aromatic nucleus

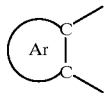

comprising at least one heteroatom.

5. Method according to claim 1, wherein the said aromatic nucleus is additionally substituted by at least one electron-withdrawing group.

6. Method according to claim 1, wherein the said aromatic nucleus is substituted by at least one electron-withdrawing group with a predominant inductive effect.

7. Method according to claim 6, wherein said electron-withdrawing group with an inductive effect is selected from the —CN and —CF$_2$R groups, where R is selected from a fluorine atom and hydrocarbon-comprising groups.

8. Method according to claim 5, wherein said aromatic nucleus is substituted by a single electron-withdrawing group.

9. Method according to claim 1, wherein said withdrawing group is in the ortho or para position with respect to the X atom to be substituted.

10. Method according to claim 1, wherein the sum of the Hammett constants of the electron-withdrawing functional groups carried by the said aromatic nucleus is between 0.10 and 1.60.

11. Method according to claim 1, wherein the sum of the Hammett constants of the substituents of the said aromatic nucleus is between 0.4 and 1.

12. Method according to claim 1, wherein the Hammett constant of each of the substituents of the said aromatic nucleus other than X is between 0.2 and 0.7.

13. Method according to claim 1, wherein the halogen/fluorine exchange reactant of the step (a) is an inorganic fluoride, in particular an alkali metal fluoride, or quaternary ammonium fluoride.

14. Method according to claim 1, wherein the amount of fluorine employed in the step (a) is between 0.8 and 1.5 times the amount of compound of formula (I).

15. Method according to claim 1, wherein the reaction of the step (a) is carried out at a temperature of 80 to 280° C.

16. Method according to claim 1, wherein the reaction mixture obtained at the end of the step (a) is charged as is in the step (b).

17. Method according to claim 1, wherein the said fluorine/cyanide exchange reactant of the step (b) comprises a cyanide selected from cyanides of metals from Groups I and II and quaternary ammonium cyanides.

18. Method according to claim 1, wherein the amount of cyanide employed in the step (b) is between 1 and 1.5 times the amount of compound of formula (III) formed in the step (a).

19. Method according to claim 1, wherein the copper content in the reaction mixture of the step (b) is $10^{-2}$ mol.l$^{-1}$ or less.

20. Method according to claim 1, wherein the amount of copper present in the reaction system of the step (b), expressed as mol, is less than or equal to one tenth of the amount of reaction product of the step (a) employed in the step (b), expressed as mol.

21. Method according to claim 1, wherein fluoride released by the fluorine/cyanide exchange reaction and optionally fluoride which has not reacted in the step (a) is isolated in the step (b) and is recycled in the step (a) as halogen/fluorine exchange reactant.

22. Method according to claim 7 wherein said hydrocarbon-comprising groups are electron-withdrawing hydrocarbon-comprising groups.

* * * * *